United States Patent [19]

Miyashita et al.

[11] Patent Number: 5,567,730
[45] Date of Patent: Oct. 22, 1996

[54] METHOD OF STABILIZING AN ω-3 UNSATURATED FATTY ACID COMPOUND

[75] Inventors: Kazuo Miyashita, Hakodate; Toru Ota, Kameda-gun; Suguru Okazaki, Koga; Masazumi Nishikawa; Kazuaki Maruyama, both of Tsukuba, all of Japan

[73] Assignee: Maruha Corporation, Chiyoda-Ku, Japan

[21] Appl. No.: 385,573

[22] Filed: Feb. 8, 1995

Related U.S. Application Data

[63] Continuation of Ser. No. 88,148, Jun. 15, 1993, abandoned.

[30] Foreign Application Priority Data

Jul. 28, 1992 [JP] Japan .................................. 4-201437

[51] Int. Cl.$^6$ ............................ A61K 31/22; A61K 31/20
[52] U.S. Cl. .................................... 514/549; 514/558
[58] Field of Search .................................. 514/549, 558; 424/554, 523; 426/602, 608

[56] References Cited

U.S. PATENT DOCUMENTS

| | | | |
|---|---|---|---|
| 4,678,808 | 7/1987 | Ward et al. | 514/560 |
| 4,826,877 | 5/1989 | Stewart et al. | 514/560 |

*Primary Examiner*—Raymond Henley, III
*Attorney, Agent, or Firm*—Pennie & Edmonds

[57] ABSTRACT

A method of stabilizing ω-3 unsaturated fatty acid compounds comprising dispersing one or more compounds selected from a group consisting of an ω-3 unsaturated fatty acid, its derivative and an oil and fat containing the ω-3 unsaturated fatty acid or the derivative in an aqueous solution, is presented. ω-3 Unsaturated fatty acids such as DHA and EPA which have been regarded as unstable can be kept under stable conditions.

8 Claims, 7 Drawing Sheets

Maruha Stamina + sardine oil milk + tune orbital tissue extract oil

# METHOD OF STABILIZING AN ω-3 UNSATURATED FATTY ACID COMPOUND

This is a continuation of application Ser. No. 08/088,148, filed Jun. 15, 1993, now abandoned.

FIELD OF THE INVENTION

This invention relates to a method of stabilizing an ω-3 unsaturated fatty acid compound.

BACKGROUND OF THE INVENTION

ω-3 Unsaturated fatty acids such as docosahexaenoic acid and eicosapentaenoic acid has been known to have various functions including inhibiting platelet aggregation, lowering a cholesterol level in blood, improving function of brain (see, Japanese Patent Laid-Open Hei 1-279827, Japanese Patent Laid-Open Hei 2-49723), and an antiallergic action. However, compared with ω-6 unsaturated fatty acids such as linolic acid, the ω-3 unsaturated fatty acid compound such as docosahexaenoic acid and eicosapentaenoic acid has an extremely inferior stability to oxidation, and it provides an unpleasant smell and taste, when it is oxidized, so it has been difficult to add it to a food, not to mention the use as a salad oil or a frying oil like safflower oil containing a large amount of linolic acid and the like. Accordingly, there have been various antioxidation means provided in order to utilize ω-3 unsaturated fatty acids such as docosahexaenoic acid and eicosapentaenoic acid as well as fats and oils containing them; the means include, for example, a process using an anti-oxidizing agent such as tocopherol and catechin, an encapsulation process using gelatin etc., and a process to fill an inactive gas. However, even by the use of the above-mentioned processes, the problem of long-term stability has not yet been cleared completely, and as for the ingestion, there are even such problems as an unpleasant feeling caused by the smell of the oxide and influence of the oxide on a human body. The antioxidation process and ingestion process for ω-3 unsaturated fatty acids such as docosahexaenoic acid and eicosapentaenoic acid as well as fats and oils containing them still have problems to be solved.

PROBLEMS TO BE SOLVED BY THE PRESENT INVENTION

The present invention is to meet the above-mentioned demand, and to embody a method to stabilize ω-3 unsaturated fatty acids such as docosahexaenoic acid and eicosapentaenoic acid as well as fats and oils containing them.

Through investigation of a method to stabilize ω-3 unsaturated fatty acids such as docosahexaenoic acid and eicosapentaenoic acid as well as fats and oils containing them, the inventors have found that ω-3 unsaturated fatty acid compounds such as docosahexaenoic acid and eicosapentaenoic acid are unexpectedly extremely stable in an aqueous system which has been detested for ω-6 unsaturated fatty acids such as linolic acid etc. since it accelerates the oxidation of ω-6 unsaturated fatty acids.

SUMMARY OF THE INVENTION

According to one aspect of the present invention, there is provided a method of stabilizing ω-3 unsaturated fatty acid compounds, comprising dispersing one or more compounds selected from a group consisting of an ω-3 unsaturated fatty acid, its derivative and an oil or fat containing the ω-3 unsaturated fatty acid or the derivative, in an aqueous solution. According to another aspect of the present invention, there is provided a method of stabilizing ω-3 unsaturated fatty acid compounds, comprising dispersing one or more compounds selected from a group consisting of an ω-3 unsaturated fatty acid, its derivative and an oil or fat containing the ω-3 unsaturated fatty acid or the derivative, in an aqueous solution by the use of a surface active agent or an emulsifying agent.

According to the present invention, ω-3 unsaturated fatty acids such as docosahexaenoic acid and eicosapentaenoic acid, which have been considered to be unstable so far, can be kept under stable conditions, and the application of this method allows the ω-3 unsaturated fatty acids to be used not only for a health drink and milk, the products shown in the following examples, but also for canned foods, bean curd and fish-paste products.

BRIEF DESCRIPTION OF THE FIGURES

The present invention may be understood more fully by reference to the following detailed description of the invention, examples of specific embodiments of the invention and the appended figures in which.

DETAILED DESCRIPTION OF THE PREFERRED EMBODIMENT

The ω-3 unsaturated fatty acid of the present invention includes, for example, docosahexaenoic acid and eicosapentaenoic acid.

The derivative of the ω-3 unsaturated fatty acid of the present invention includes, for example, its salts, amides, phospholipids, monoglycerides, diglycerides and various esters such as ethyl esters and sucrose esters, as well as fatty acids, phospholipids and triglycerides extracted from natural fats and oils.

According to the present invention, the ω-3 unsaturated fatty acid can be dispersed in an aqueous solution optionally using a surface active agent or an emulsifying agent. As the surface active agent and the emulsifying agent, Tween 20, a sucrose fatty ester, a sorbitan fatty ester, lecithin and monoglyceride are especially preferable.

When no surface active agent nor emulsifying agent is used, the amount of the ω-3 unsaturated fatty acid to be added to the aqueous system to allow the stabilization, is 0.0001–0.3 (w/v) %, preferably 0.0001–0.1 (w/v) %.

When a surface active agent or an emulsifying agent is used, the amount of the ω-3 unsaturated fatty acid to be added to the aqueous system to allow the stabilization, is 0.0001–7 (w/v) %, preferably 0.0001–1 (w/v) %. The adequate amount of the surface active agent and that of the emulsifying agent to be added in such a case, is 0.01–2 (w/v) %.

In the stabilization method of the present invention, a water soluble or oil soluble anti-oxidizing agent, or a clathrate inclusion compound such as cyclodextrin can be used together with the surface active agent or the emulsifying agent.

The stabilization method of the present invention can be applied to pharmaceuticals including a health drink, and such foods as canned foods, bean curd, and fish-paste products.

The following examples are merely illustrative of the invention, and are not intended to limit the same.

EXAMPLES

Example 1

Figure 1:
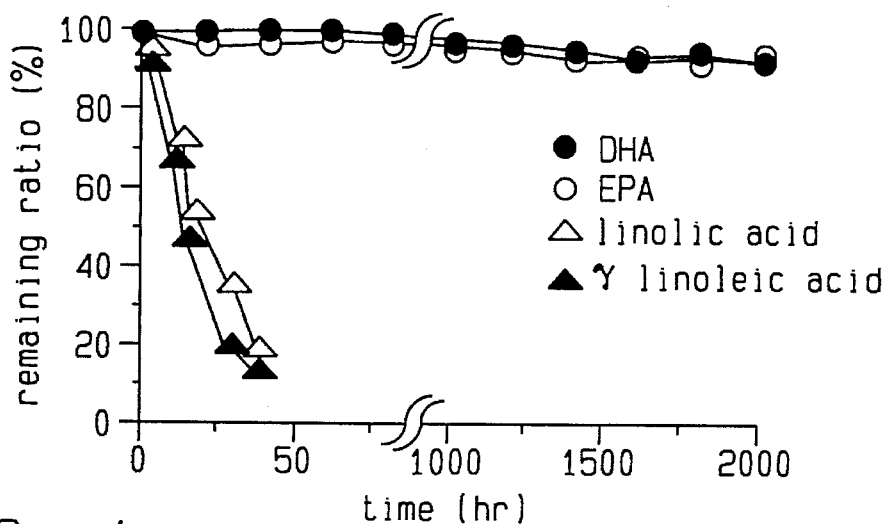
FIG. 1 is a graph showing the stability of docosahexaenoic acid, eicosapentaenoic acid, linolic acid and γ-linolenic acid stored in an aqueous system.

Docosahexaenoic acid (hereinafter referred to as DHA: 99%), eicosapentaenoic acid (hereinafter referred to as EPA: 99%), linolic acid (hereinafter referred to as LA: 99%), and γ-linolenic acid (99%) were dispersed in 0.05M phosphate buffer solution (pH 7.4) in a concentration of 1 mM respectively, and ascorbic acid-$Fe^{2+}$ aqueous solution having lipid peroxidation acceleration function was added (0.5%), and the stability to oxidation at 37° C. was examined by storing it under a dark condition. Evaluation was carried out in terms of the remaining ratio of the fatty acid, by sampling the lipid at a certain time interval, which was analyzed by gas chromatography. The results show, as in FIG. 1, that the ω-3 unsaturated fatty acids DHA and EPA had a remaining ratio in terms of the fatty acid, of over 95% even after 2000 hours, while the ω-6 unsaturated fatty acids LA and γ-linolenic acid reduced their remaining ratios to less than 20% within about 30 hours. Accordingly, it was confirmed that ω-3 unsaturated fatty acids such as DHA and EPA were stable to oxidation in an aqueous system.

Example 2

Figure 2:
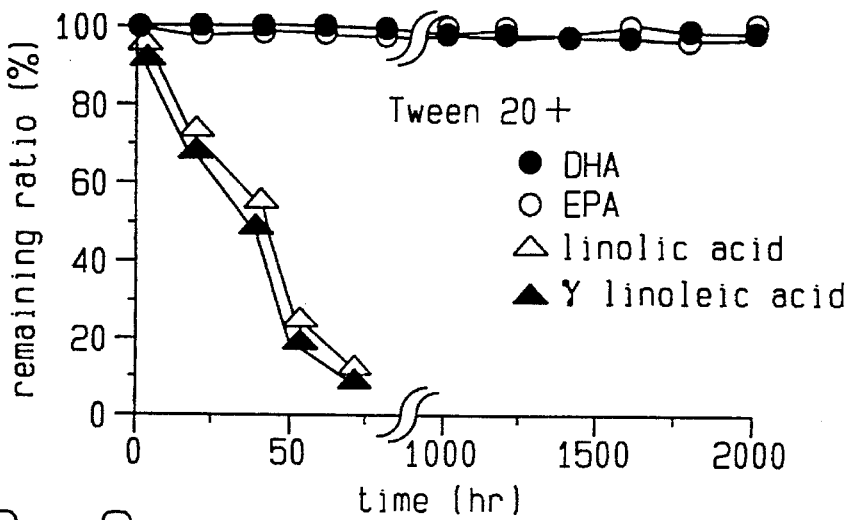
FIG. 2 is a graph showing the stability of docosahexaenoic acid, eicosapentaenoic acid, linolic acid and γ-linolenic acid stored in an aqueous system in the presence of Tween 20.
Figure 3:
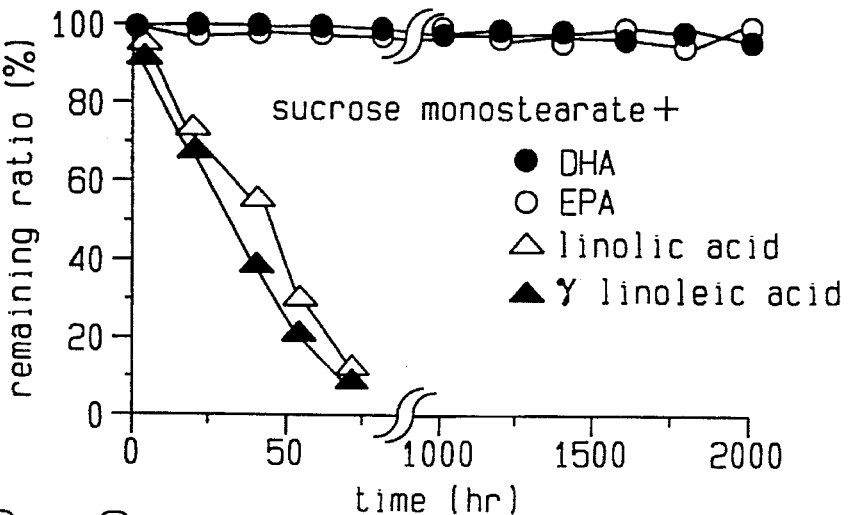
FIG. 3 is a graph showing the stability of docosahexaenoic acid, eicosapentaenoic acid, linolic acid and γ-linolenic acid stored in an aqueous system in the presence of sucrose monostearate.

In the same manner as in Example 1, DHA, EPA, LA, and γ-linolenic acid were dissolved in 0.05M phosphate buffer solution (pH 7.4) containing 1 (w/v) % Tween 20 or 1 (w/v) % sucrose monostearate in a concentration of 5 mM respectively, and stabilization tests were carried out. From the results shown in FIG. 2 and FIG. 3, DHA and EPA were found to be very stable, since they showed a remaining ratio of almost 100% respectively even after 2000 hours in either case using Tween 20 or sucrose monostearate. However, LA and γ-linolenic acid had a remaining ratio of 20% respectively after 50 hours or so, and thus they were found to have problems in their stability to oxidation in an aqueous system.

Example 3

Figure 4A:
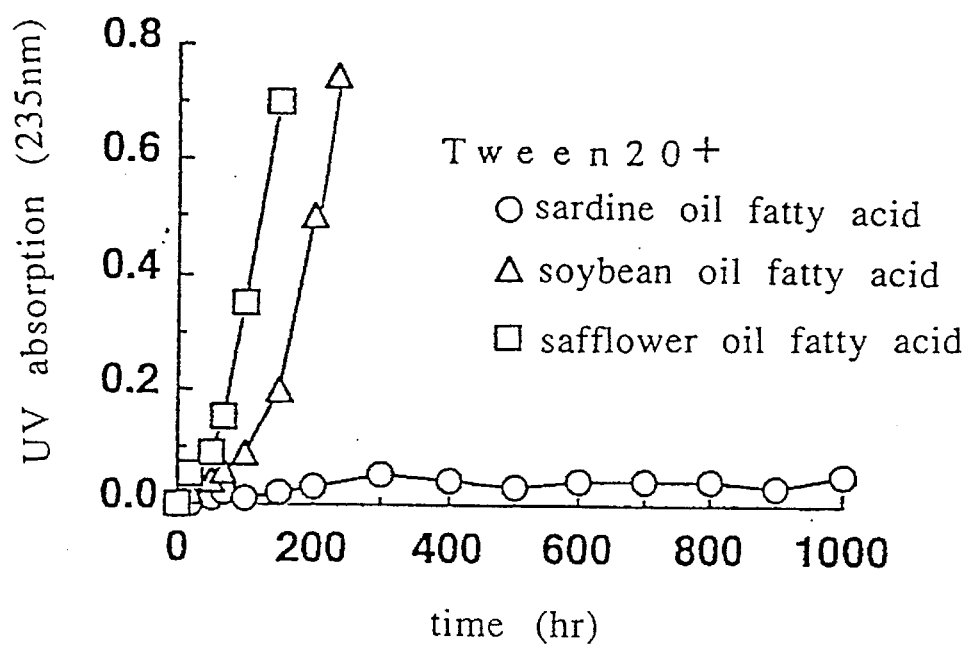
FIG. 4a is a graph showing the variation in UV absorption of sardine oil fatty acid, soybean oil fatty acid, and safflower oil fatty acid stored in an aqueous system in the presence of Tween 20.
Figure 4B:
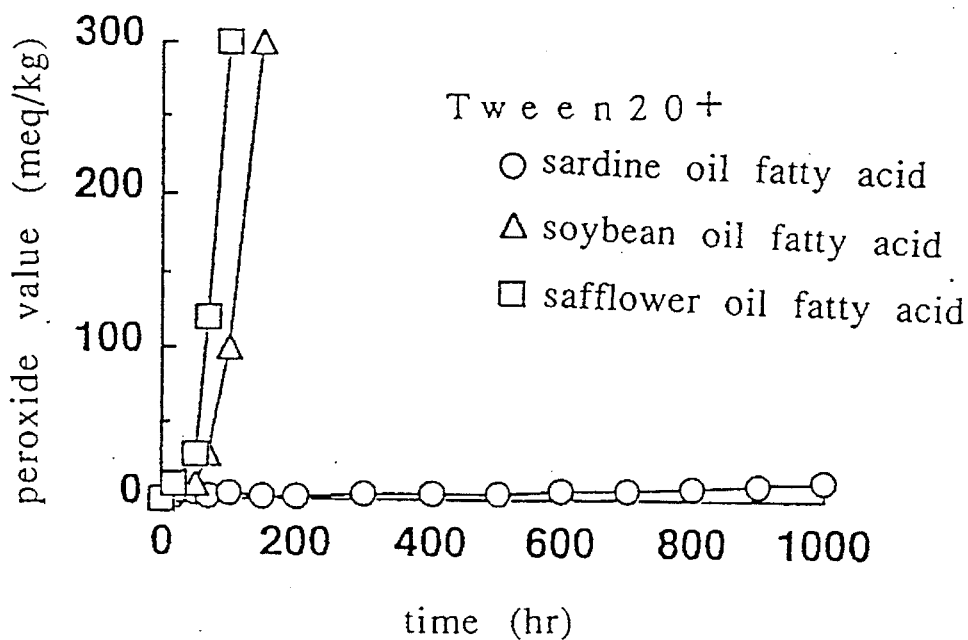
FIG. 4b is a graph showing the variation of peroxide value of sardine oil fatty acid, soybean oil fatty acid, and safflower oil fatty acid stored in an aqueous system in the presence of Tween 20.
Figure 5A:
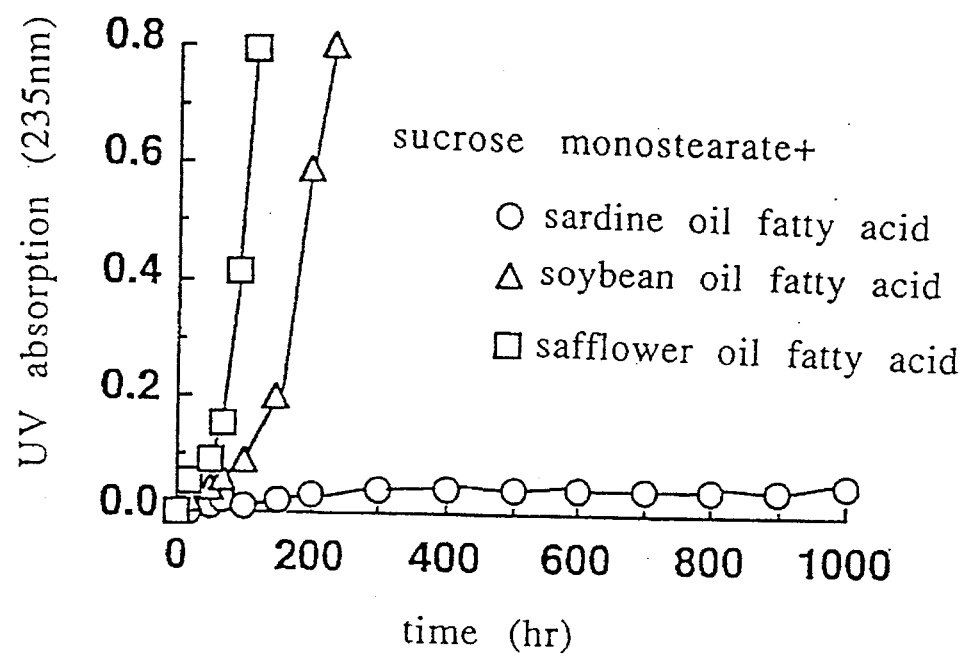
FIG. 5a is a graph showing the variation in UV absorption of sardine oil fatty acid, soybean oil fatty acid, and safflower oil fatty acid stored in an aqueous system in the presence of sucrose monostearate.
Figure 5B:
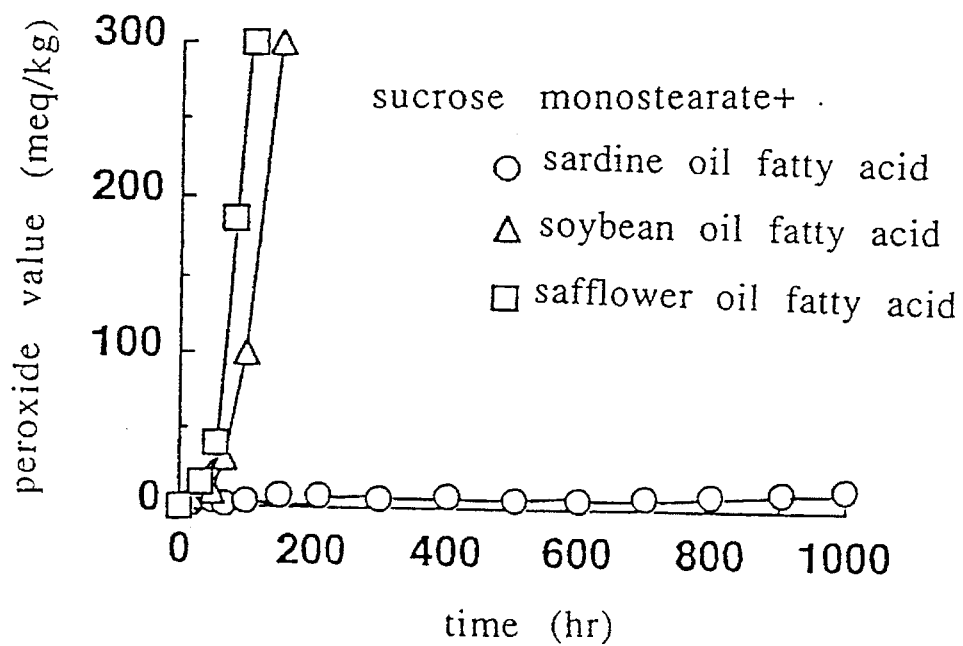
FIG. 5b is a graph showing the variation of peroxide value of sardine oil fatty acid, soybean oil fatty acid, and safflower oil fatty acid stored in an aqueous system in the presence of sucrose monostearate.

Sardine oil, soybean oil and safflower oil were respectively hydrolyzed by the use of lipase to provide fatty acids, then the examination was carried out in the same manner as in Example 2. That is, the sardine oil fatty acid, soybean oil fatty acid and safflower oil fatty acid were dissolved in 0.05M phosphate buffer solution (pH 7.4) containing 1 (w/v) % Tween 20 or 1 (w/v) % sucrose monostearate in a concentration of 0.15% respectively, and stabilization test was carried out. The judgment was done by the measurement of UV absorption (at 238 nm) and a peroxide value (hereinafter referred to as POV). From the results shown in FIGS. 4 and 5, the sardine oil fatty acid was found to be stable in the aqueous system in both of the cases using Tween 20 and using sucrose monostearate, since no remarkable increase was found in the UV absorption nor in the POV after 1000 hours. However, the soybean oil fatty acid and the safflower oil fatty acid showed drastic peroxidation of lipid in 100 hours or so. The change was remarkable especially in safflower oil fatty acid, and this was considered to be attributable to the deterioration of ω-6 unsaturated fatty acids such as LA etc. from the results of the Examples 1, 2 and 3.

Example 4

Figure 6A:
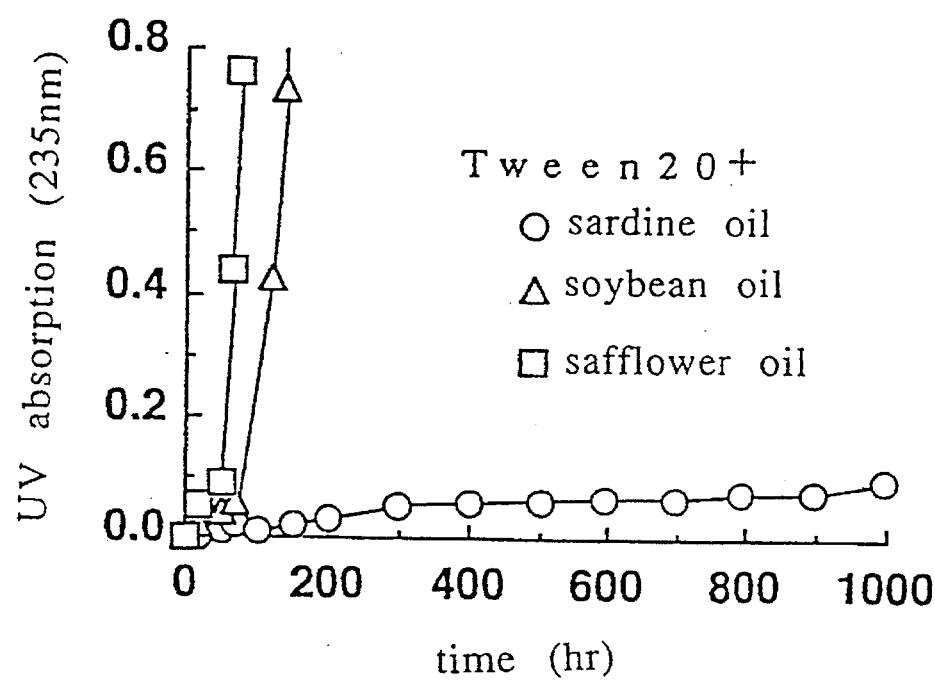
FIG. 6a is a graph showing the variation in UV absorption of sardine oil, soybean oil, and safflower oil stored in an aqueous system in the presence of Tween 20.
Figure 6B:
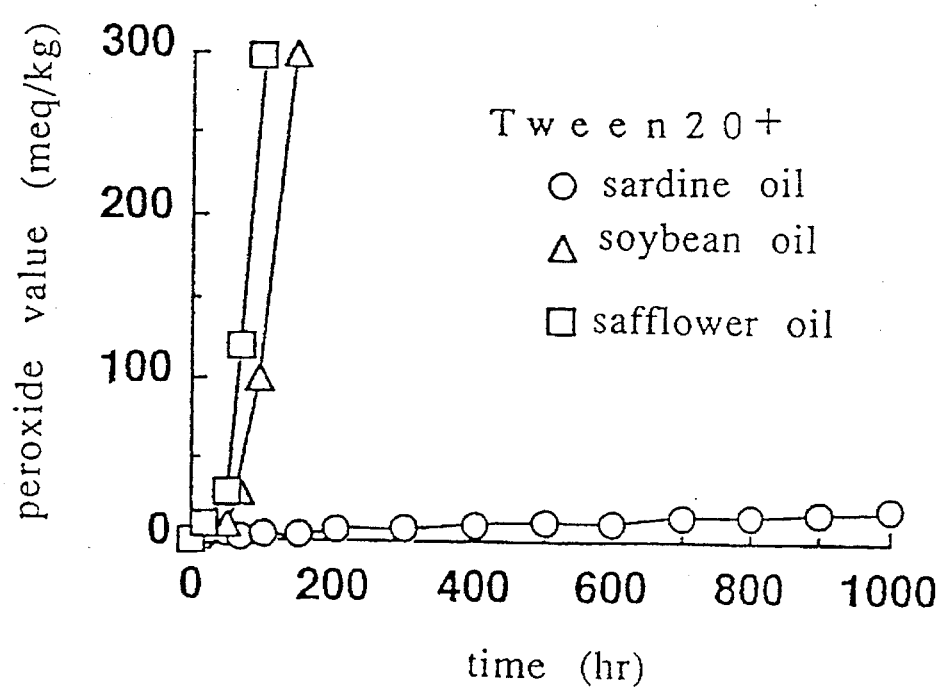
FIG. 6b is a graph showing the variation in peroxide value of sardine oil, soybean oil, and safflower oil stored in an aqueous system in the presence of Tween 20.
Figure 7A:
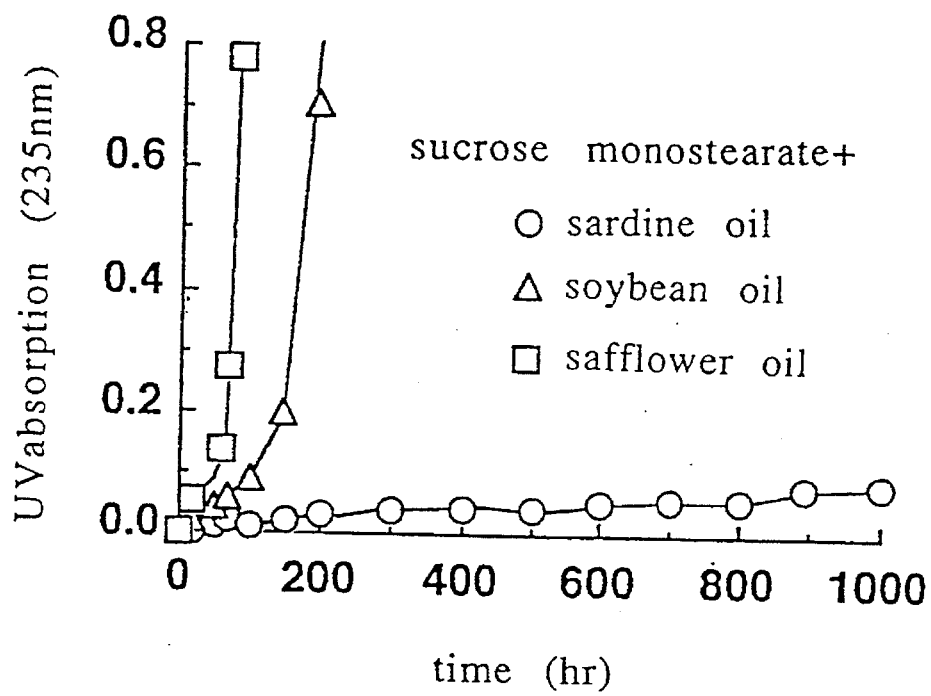
FIG. 7a is a graph showing the variation in UV absorption of sardine oil, soybean oil, and safflower oil stored in an aqueous system in the presence of sucrose monostearate.
Figure 7B:
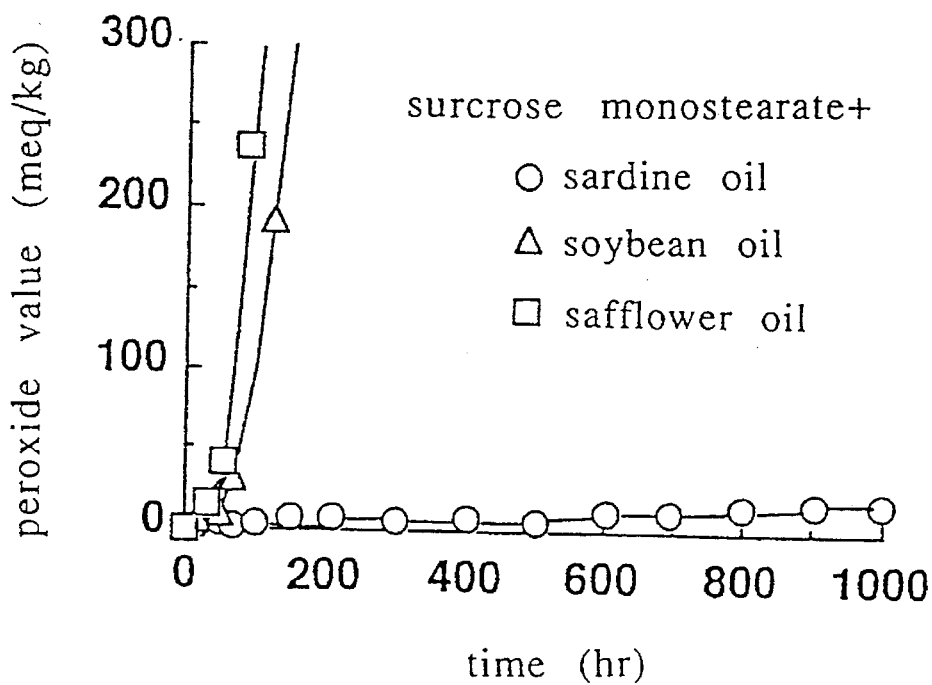
FIG. 7b is a graph showing the variation in peroxide value of sardine oil, soybean oil, and safflower oil stored in an aqueous system in the presence of sucrose monostearate.

The examination was carried out in the same manner as in Example 3, using the sardine oil, soybean oil and safflower oil in the oil form. That is, the sardine oil, soybean oil and safflower oil were dissolved in 0.05M phosphate buffer solution (pH 7.4) containing 1 (w/v) % Tween 20 or 1 (w/v) % sucrose monostearate in a concentration of 0.15% respectively, and stabilization test was carried out. From the results shown in FIGS. 6 and 7, the sardine oil was found to be stable after 1000 hours in the aqueous system in either case using Tween 20 or sucrose monostearate, since no remarkable increase was found in the UV absorption nor in the POV. However, the soybean oil and the safflower oil showed drastic peroxidation of lipid in 80 hours or so.

Example 5

Figure 8:
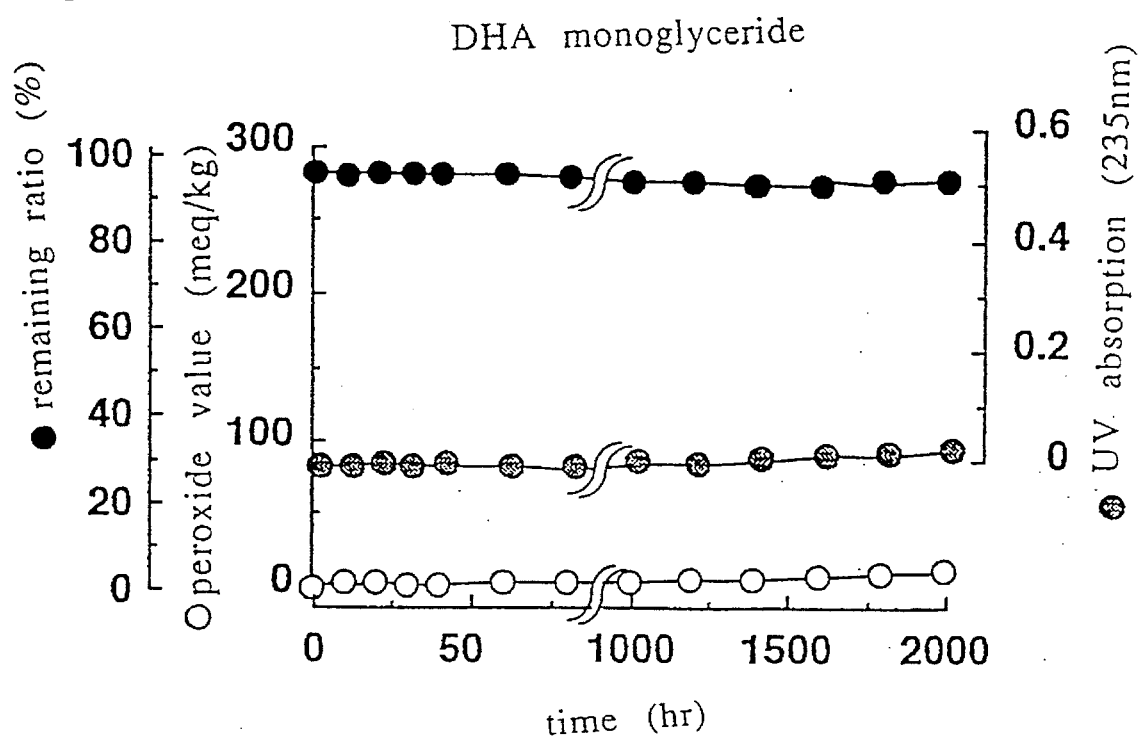
FIG. 8 is a graph showing the stability of docosahexaenoic acid monoglyceride in an aqueous system.

Esterification reaction was carried out by using DHA (99%) and glycerine, and DHA monoglyceride was then obtained by molecular distillation process. The monoglyceride itself has been widely used as an emulsifying agent. Accordingly, the stability of DHA monoglyceride, when it was also used as the emulsifying agent, was examined. The DHA monoglyceride was dissolved in 0.05M phosphate buffer solution (pH 7.4) in a concentration of 0.2%, and a stability test was carried out. The measurement of UV and POV shown in the Example 3 was carried out with time, and at the same time, the remaining ratio of DHA was examined. As the result, DHA monoglyceride was found to be very stable, as shown in FIG. 8, and it showed a good remaining ratio as well as good UV and POV values over the period of 2000 hours or more.

Example 6

Preparation of a health drink containing DHA

The stability of DHA added to a health drink was examined.

Figure 9:
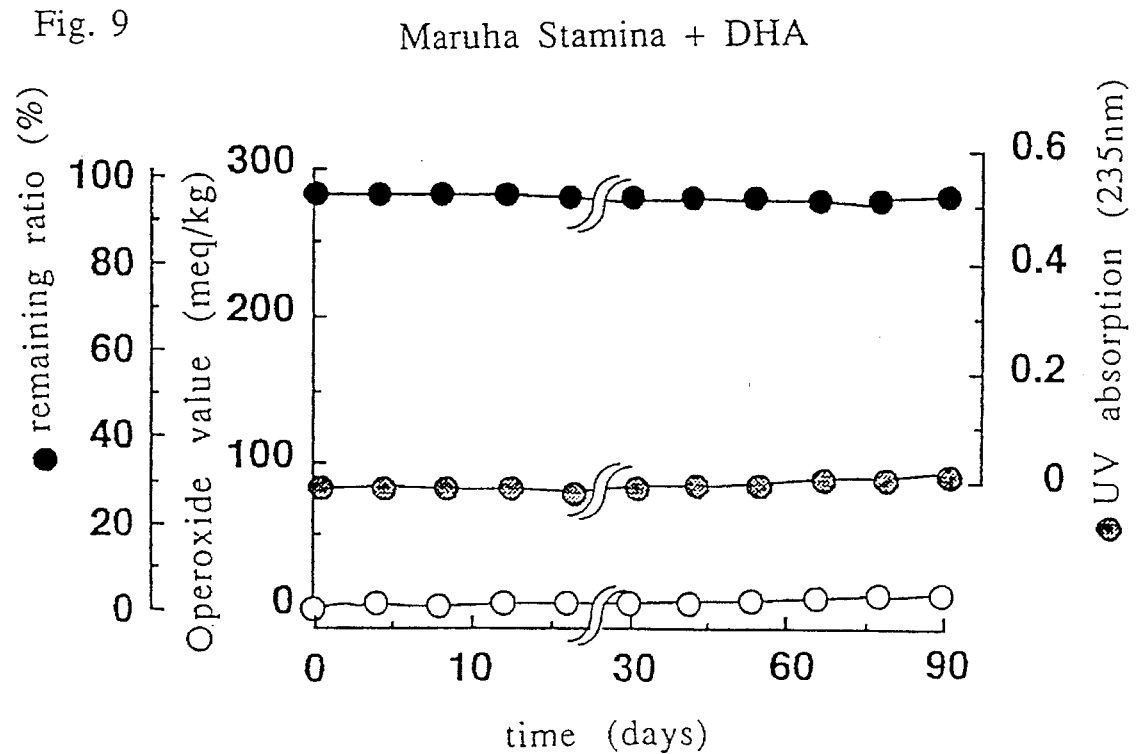
FIG. 9 is a graph showing the stability of docosahexaenoic acid added to a health drink.
Figure 10:
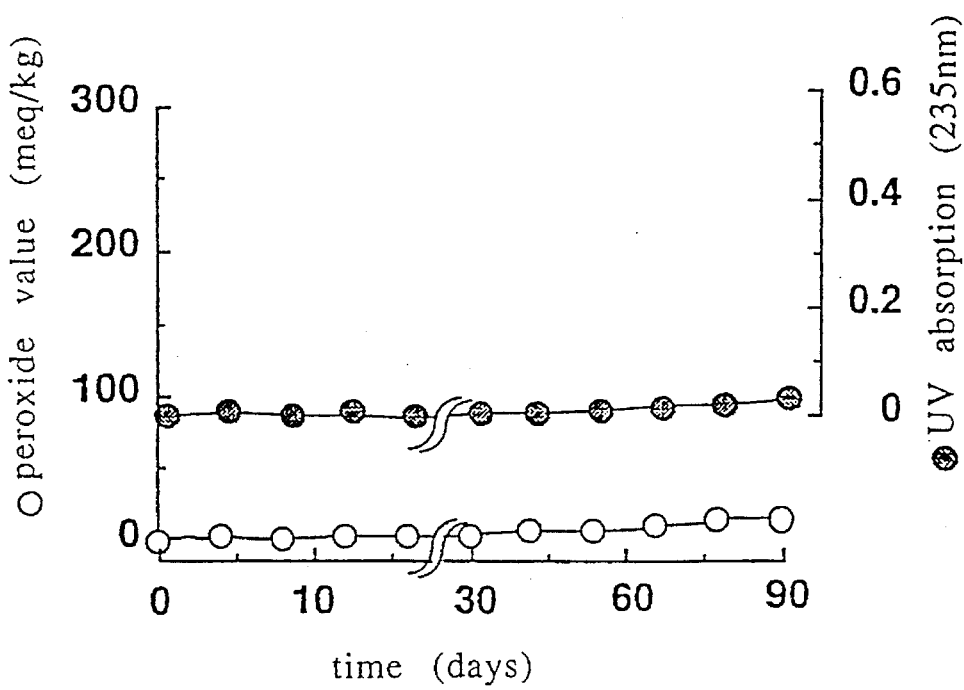
FIG. 10 is a graph showing the stability of sardine oil added to a health drink.

As a health drink, Maruha Stamina (produced by Taiyo Fishery Co., Ltd.) was used, and DHA and sucrose monostearate were added in a concentration of 0.03% and 1% respectively, then preservation test was carried out by preserving it in a dark place at room temperature. The results in FIG. 9 showed that DHA had a high remaining ratio after 90 days, and showed no variation in POV nor UV. Similar examination was carried out on Maruha Stamina (produced by Taiyo Fishery Co., Ltd.) containing sardine oil, and both POV and UV showed good values (see FIG. 10). Sampling test of the health drink was carried out by a panel of 10 men and 10 women before and 90 days after the preservation, but only a few felt a strange taste or a strange smell even after 90 days, as shown in Table 1.

TABLE 1

| Sensory Evaluation | Maruha Stamina + DHA | | Maruha Stamina + sardine oil | |
|---|---|---|---|---|
| | before preservation | after 90 days | before preservation | after 90 days |
| feel no strange taste nor smell | 19 | 18 | 18 | 18 |
| feel a little strange taste and smell | 1 | 1 | 2 | 1 |
| feel strange taste and smell | 0 | 1 | 0 | 1 |

Example 7

Preparation of milk containing DHA

The stability of DHA added to milk was examined.

Figure 11:
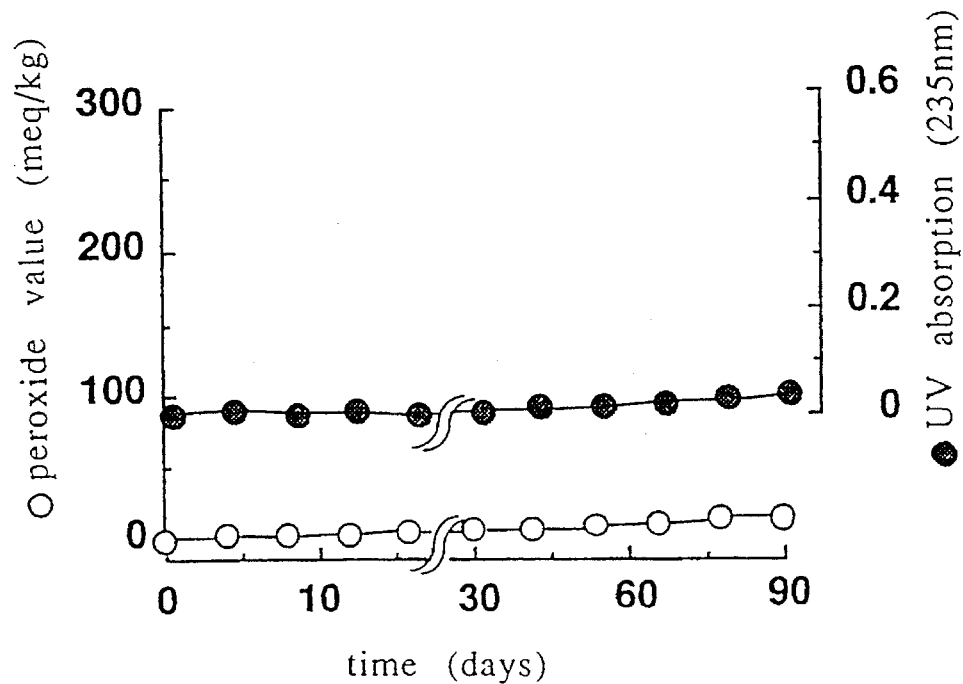
FIG. 11 is a graph showing the stability of tuna orbital tissue extract oil added to milk.

Tuna orbital tissue extract oil (0.03% in terms of DHA), sucrose monostearate and lecithin were added to milk in a concentration of 0.1%, 0.9% and 0.2% respectively. After sterilization, it was packaged in a germ-free pack, and preservation test was carried out by preserving it at room temperature. From the results shown in FIG. 11, no variation of POV nor UV was observed even after 90 days. Sampling test of the milk was carried out by a panel of 15 men, 10 women and 10 children before and 90 days after the preservation, but only a few felt a strange taste or a strange smell even after 90 days, as shown in Table 2.

TABLE 2

| Sensory Evaluation | Milk + Tuna orbital tissue extract oil | | | |
|---|---|---|---|---|
| | before preservation | after 30 days | after 60 days | after 90 days |
| feel no strange taste nor smell | 34 | 34 | 33 | 32 |
| feel a little strange taste and smell | 1 | 1 | 2 | 2 |
| feel strange taste and smell | 0 | 0 | 0 | 1 |

We claim:

1. A method of oxidatively stabilizing omega-3 unsaturated fatty acid compounds comprising dispersing one or more omega-3 unsaturated fatty acid compounds selected from the group consisting of an omega-3 unsaturated fatty acid, an acid derivative thereof and an oil or fat containing an omega-3 unsaturated fatty acid or acid derivative thereof in an aqueous solution without the use of an exogenously added emulsifier.

2. The method of claim 1, further comprising excluding said aqueous solution from exposure to light.

3. The method of claim 1, wherein the omega-3 fatty acid compound is docosahexaenoic acid or eicosapentaenoic acid.

4. The method of claim 1, wherein the acid derivative is selected from the group consisting of a salt, an amide, a phospholipid, a monoglyceride, a diglyceride, a triglyceride, a lower alkyl ester and a sucrose ester.

5. A comestible or pharmaceutical composition comprising one or more oxidatively stabilized compounds selected from the group consisting of an omega-3 unsaturated fatty acid, an acid derivative thereof and an oil or fat containing an omega-3 unsaturated fatty acid or acid derivative thereof, wherein said compound(s) is/are dispersed in an aqueous solution without the use of an exogenously added emulsifier, so that said compound(s) is/are oxidatively stabilized.

6. The composition of claim 5, wherein the aqueous solution is excluded from exposure to light.

7. The composition of claim 5, wherein the omega-3 fatty acid compound is docosahexaenoic acid or eicosapentaenoic acid.

8. The composition of claim 5, wherein the acid derivative is selected from the group consisting of a salt, an amide, a phospholipid, a monoglyceride, a diglyceride, a triglyceride, a lower alkyl ester and a sucrose ester.

* * * * *